United States Patent [19]

Carlo et al.

[11] 4,413,057

[45] Nov. 1, 1983

[54] GROUP B STREPTOCOCCAL CAPSULAR POLYSACCHARIDES

[75] Inventors: Dennis J. Carlo, Bound Brook; Karl H. Nollstadt, Clark; Thomas H. Stoudt, Westfield; Robert Z. Maigetter, Summit, all of N.J.

[73] Assignee: Merck & Co., Inc., Rahway, N.J.

[21] Appl. No.: 343,305

[22] Filed: Mar. 16, 1981

Related U.S. Application Data

[63] Continuation-in-part of Ser. No. 140,031, Apr. 14, 1980, abandoned.

[51] Int. Cl.$^3$ ..................... C12P 19/04; C08B 37/00; A61K 39/02
[52] U.S. Cl. ..................... 435/101; 424/92; 424/88; 536/127
[58] Field of Search .................. 424/88–89, 424/92; 536/1, 4, 124; 435/72, 84, 101

[56] References Cited

U.S. PATENT DOCUMENTS 4,207,414 6/1980 Kasper ..................... 536/1

OTHER PUBLICATIONS

Baker, C., J. Infectious Diseases, vol. 136, pp. 137–152, 1977.
Anthony, B., Ann. Rev. Med., vol. 28, pp. 41–57, 1977.
Wilkinson, H. W., Ann. Rev. Microbiol., vol. 32, pp. 355–367, 1978.
Tai, J., et al., J. Exp. Med., vol. 149, pp. 58–66, 1979.
Kasper, D., et al., J. Immunology, vol. 121, pp. 1096–1105, 1978.
Baker, C., et al., J. Experimental Medicine, vol. 143, pp. 258–270, 1976.
Wittner, M., et al., J. Bacteriology, vol. 89, pp. 398–402, 1965.
Russell, H., et al., J. Immunology, vol. 109, pp. 90–96, 1972.

*Primary Examiner*—Blondel Hazel
*Attorney, Agent, or Firm*—Gabriel Lopez; Hesna J. Pfeiffer

[57] ABSTRACT

Group B Streptococcus type-specific polysaccharides types $I_1$, $I_b$, II and III have been obtained from strains grown in a modified soy bean and yeast medium. These polysaccharides are useful as active or passive streptococcal vaccines.

8 Claims, No Drawings

GROUP B STREPTOCOCCAL CAPSULAR POLYSACCHARIDES

CROSS-REFERENCE

This is a continuation-in-part of U.S. Ser. No. 140,031, filed Apr. 14, 1980 now abandoned.

BACKGROUND OF THE INVENTION

Group B *Streptococcus* (*Streptococcus agalactiae*) has recently been identified as the leading cause of meningitis among neonates and young infants. A conservative estimation [C. J. Baker, *J. Infectious Diseases,* 136, No. 1, 137 (1977)] indicates that about 12,000 to 15,000 infants will be affected annually. Half of them will die. Those who survive may develop fatal neurological sequelae that often progress too far to be arrested by antibiotic treatments. For this reason, the immunological, preventive approach as embodied in vaccination of Group B streptococcal type-specific polysaccharides has evolved as one of the most important aspects for future control of the disease. In addition, antibody specific to type $I_a$ *Streptococcus agalactiae* has recently been found in the glands of bovine immunized with killed or live vaccine, indicating that Group B streptococcal type-specific polysaccharides may be important in vaccination against mastitis in dairy mammals, for example, dairy cattle.

Group B streptococcal antigens are generally classified into five serotypes ($I_a$, $I_b$, $I_c$, II and III) based on capillary precipitin tests with hydrochloric acid-extracted antigens and type-specific hyperimmune rabbit antisera.

Although later studies have shown chemical compositions indicating structures quite different from those reported originally, the same serological classification, i.e., $I_a$, $I_b$, $I_c$, II and III for streptococcal polysaccharides, are still being followed. For example, type-specific polysaccharides isolated via HCl-treatment of whole organisms were reported to contain rhamnose, glucosamine, and galactose, while type-specific polysaccharides prepared by TCA (trichloroacetic acid) extraction contained an additional antigenic determinant, sialic acid. Furthermore, structural difference may also arise from variation of fermentation conditions. Thus Group B Streptococcal polysaccharides isolated by identical methods from organisms grown in the presence of excess glucose has been found to contain no rhamnose as previously reported.

The present invention is related to novel Group B streptococcal polysaccharide types $I_a$, $I_b$, II and III, all of which contain galactose, glucosamine, glucose, and sialic acid. They are structurally distinguishable from those reported earlier as a result of variation in fermentation conditions, methods of isolation and purification.

Accordingly, it is an object of the present invention (1) to provide highly purified antigenic Group B streptococcal polysaccharide types $I_a$, $I_b$, II and III of novel structures; (2) to provide a vaccine for neonates or infants against Group B Streptococcus infections, for example, meningitis, containing at least one of the novel Group B streptococcal polysaccharides; (3) to provide a method for the prevention of neonatal diseases induced by Group B Streptococcus by vaccination of pregnant women or women of childbearing age; (4) to provide a novel method for the isolation and purification of the Group B streptococcal polysaccharides; (5) to provide a vaccine containing one or more of the type-specific Group B streptococcal polysaccharides for protection against masititis in dairy mammals; (6) to provide a method for protection against Group B Streptococcus infections by passive vaccination of patients with impaired immune system; and (7) to provide a method for protection against mastitis in dairy mammals by passive vaccination.

DETAILED DESCRIPTION OF THE INVENTION

Antigenic Group B streptococcal polysaccharide types $I_a$, $I_b$, II and III have been isolated having the specifications shown below in Table I based on dry weight analysis.

TABLE I

SPECIFICATION OF GROUP B STREPTOCOCCUS TYPE-SPECIFIC POLYSACCHARIDES

| | $I_a$ | $I_b$ | II | III |
|---|---|---|---|---|
| $K_d$ | 0.3–0.4 | 0.3–0.4 | 0.3–0.4 | 0.5–0.6 |
| % PRT | 0.5 | 1.0–2.1 | 0.5 | 1.2–5.0 |
| % NA | 0.2 | 0.5 | 0.2 | 0.1–0.5 |
| % P | 0.1–0.5 | 0.1–0.5 | 0.1–0.5 | 0.5 |
| % HXA | 13.7–22.5 | 12.0–18.0 | 10.0–15.8 | 20.0–27.0 |
| % OAC | 0.5 | 0.5–1.0 | 1.0 | 0.5 |
| % HEX | 35.0–40.0 | 50.0–62.5 | 35.0–45.3 | 45.0–55.0 |
| % GLU | 14.1–20.7 | 30.0–41.6 | 15.0–22.1 | 10.0–17.4 |
| % SA | 25.0–30.0 | 7.0–16.6 | 20.6–25.0 | 25.0–35.0 |
| % MP | 0.5–1.0 | 1.4 | 2.0–5.0 | 0.5–1.0 |

$K_d$ = partition coefficient in Sepharose 4B gel chromatography
PRT = Protein
NA = Nucleic Acid
P = Phosphorus
HXA = Hexosamines (glucosamine)
OAC = O—acetates
HEX = Hexoses (including galactose and glucose in the ratio of 2:1)
GLU = Glucose
SA = Sialic Acid
MP = Methylpentose The most purified antigens of this invention have the following analyses. In all cases, the hexosamine is glucosamine and the hexoses are galactose and glucose. $K_D$ values are as determined on Sepharose 4B by gel filtration.

Type $I_a$ (product No. 11059-113): 42.9% hexose, 27.6% hexaosamine, 29.3% sialic acid; $K_D = 0.22$ Type $I_b$ (product No. 11059-193): 42.6% hexose, 18.3% hexosamine, 26.8% sialic acid, $K_D = 0.35$ Type II (product No. 11059-176): 50.9% hexose, 14.2% hexosamine, 23.9% sialic acid, $K_D = 0.44$ Type III (product No. 11059-179): 39.9% hexose, 23.3% hexosamine, 28.7% sialic acid, $K_D = 0.59$.

These type-specific antigens can therefore be defined as consisting essentially of polysaccharides of varying composition and molecular weights.

Type $I_a$ is composed of hexose, glucosamine, and sialic acid in the approximate molar ratio 3:1:1, having a molecular weight of about $0.8 \times 10^6$ daltons.

Type $I_b$ contains the same components in the approximate molar ratio 3:1:1, having a molecular weight of about $0.5 \times 10^6$ daltons.

Type II contains the same components in the approximate molar ratio 5:1:1, having a molecular weight of about $0.5 \times 10^6$ daltons.

Type III contains the same components in the approximate molar ratio 3:1:1, having a molecular weight of about $0.15 \times 10^6$ daltons.

The purified type-specified polysaccharides be they type $I_a$, $I_b$, II or III, are composed of galactose, glucosamine, glucose and sialic acid. Very small amounts of protein, nucleic acid, phosphorus, uronic acid and acetate are also present.

The polysaccharides can be isolated from any group B type-specific strain, but preferably from the following strains which are on unrestricted deposit in the American Culture Collections (ATCC).

| Type | Merck No. | ATCC No. |
|------|-----------|----------|
| $I_a$ | MB-4052 | 31,574 |
| $I_b$ | MB-4053 | 31,575 |
| II | MB-4055 | 31,576 |
| III | MB-4082 | 31,577 |
|  | MB-4316 (M 732) | 31,475 |

The most preferable strain for type III is M-732.

The preparation of antigenic polysaccharides generally comprises (1) inoculating the bacteria into a modified HySoy nutrient medium containing an excess amount of glucose (about 2.5 to 5% by weight); (2) separating the cell paste from the supernatant after phenolizing the fermentation broth; (3) isolating the crude type-specific polysaccharide either by chemical precipitation or by precipitation after enzyme digestion; and (4) purifying the crude polysaccharides by ammonium or sodium sulfate precipitation (types $I_a$ and $I_b$ only) followed by, if desired, column chromatography with an appropriate gel material as the stationary phase. The commonly used gel materials including Bio-Gel P-300, sepharose 4B, Sepharose 6B, Whatman's DEAE-cellulose (DE-52) or the like are found to be satisfactory.

Inoculation of the bacteria is accomplished by culturing a Group B Streptococcus type-specific strain, for example, MB-4055, (type II, ATCC No. 31576) in an inoculum medium such as Fluid Thioglycollate Medium (FTM). The FTM culture obtained is in turn used to inoculate a second inoculum medium which is free of animal protein and contains the necessary nutrients for the growth of the bacteria. For example, the preferred medium contains about 15 to 25 g per liter Hysoy (Humko Sheffield), about 5 to 15 g per liter Amberex 1003 (Amber), about 2.5 to 7.5 g per liter sodium chloride or potassium chloride, about 1 to 5 g liter potassium or sodium phosphate dibasic ($K_2HPO_4$ or $Na_2HPO_4$), about 0.01 g per liter phenol red and about 10 to 50 g per liter glucose in distilled water at pH 6 to 8, preferably 6.8 to 7.4. After a subsequent 9-liter inoculation, the culture which is assured of its purity according to conventional methods (see Example 1, infra), is inoculated for the large scale production fermentation. The production medium is essentially the same as the inoculum medium except that phenol red is displaced with 8% UCON LB 625 solution (see Table II, for definition) to prevent foam formation.

The more preferable medium is the medium which contains about 20 g per liter HySoy, about 5 g per liter sodium chloride, about 2.5 g per liter potassium phosphate dibasic, about 10 g per liter Amberex 1003 and about 25 g per liter (about 2.5% by weight) glucose in apyrogenic water at pH 6.9 to 7.4.

More specifically, the most preferable medium for type III polysaccharide contains the same amount of ingredients as described above. However, a solution of HySoy and Amberex 1003 (yeast extract) in about 50 ml of distilled water is dialyzed first with a molecular weight cut-off at about 12,000 to 14,000 before the resulting dialysate is mixed with other components, diluted to about 750 to 1000 ml with apyrogenic water, and adjusted to pH 7.2 before sterilization.

Generally the fermentation is conducted at about 34° to 39° C., preferably at 37° C., until the fermentation is complete, usually from about 3 hours to about 48 hours. Under optimum conditions, the fermentation is over within 24 hours.

After the fermentation is complete, it is stopped by addition of about 0.5 to 2.0% by weight of phenol followed by collection of the cells via centrifugation or filtration, preferably by centrifugation. In most cases, the cell paste is discarded except where enzymatic digestion is used to prepare polysaccharide type $I_a$ or $I_b$ from the cells (see Example 3, infra). The preferable method involves (1) treating the supernatant or filtrate with a strong ionic salt such as calcium chloride, sodium sulfate, sodium chloride, or potassium chloride, preferably calcium chloride. (2) diluting the solution with a lower alkanol such as methanol, ethanol, propanol, or butanol, preferably ethanol (20 to 50% by volume) to precipitate most of the inactive impurities such as nucleic acids; and (3) precipitating from the supernatant obtained above the desired crude type-specific polysaccharide by addition of a water-miscible lower alkanol, preferably ethanol (35 to 75% by volume).

The most preferable conditions for removal of impurities and precipitations of the crude type-specific polysaccharides including types $I_a$, $I_b$, II and III are as follows:

| Removal of Impurities | Precipitation of Crude Polysaccharide |
|-----------------------|---------------------------------------|
| 0.1M $CaCl_2$ in 40–44% by volume aqueous ethanol | $CaCl_2$ (ca. 0.07M) in 44–61% by volume aqueous ethanol |

Although each crude type-specific polysaccharide may be precipitated under substantially similar conditions as shown above, further purifications requires different procedures. Crude types $I_a$ and $I_b$ polysaccharides are further purified by (1) suspension in an appropriate amount of an aqueous solution of an inert salt, for example, about 0.5% to 5% by weight of aqueous sodium acetate or ammonium acetate or the like, preferably 1% by weight aqueous sodium acetate; (2) removal of insoluble impurities by centrifugation or filtration; and (3) saturation of the supernatant with an inert salt such as sodium sulfate, potassium sulfate, or ammonium sulfate, preferably ammonium sulfate, to salt out the semi-purified polysaccharide.

The semi-purified polysaccharide types $I_a$ and $I_b$ are subsequently purified by gel chromatography. Any commonly used gels for chromatography can be used. For example, dextran gels, polyacrylamide gels, agarose gels, macroreticular polystyrene gels, cross-linked polymethylmetaacrylate gels, Bio-gel p-300 (Bio Rad Laboratories, Richmond, Calif.), and Sepharose ® 4B or 6B (Pharmacia Fine Chemicals). The preferred gel for isolating types $I_a$ and $I_b$ is Sepharose ® 6B or 4B. Generally the semi-purified material is extracted with a minimum amount of about 0.5 to 2.5% aqueous sodium acetate, preferably about 1% by weight aqueous sodium acetate. After centrifugation, the clear supernatant is eluted with an aqueous solution of about 0.5 to 2.5% (preferably 1%) by weight sodium acetate, containing about 0.02% by weight sodium borate, sodium azide or other preservatives. The pH of the eluant is preadjusted to about 7.0. Active fractions determined by the Ouchterlony double immunodifussion technique are combined and the pooled material is concentrated to an appropriate volume at a moderate temperature preferably at 25° C. To obtain the highly purified polysaccharide, the concentrate is first dialyzed against distilled water for about 4 hours. A second dialysis against 0.01 to 0.03% by weight aqueous sodium acetate, preferably 0.02%, is conducted at about 4° C. for about 10 to 48 hours or until the dialysis is substantially complete. The dialyzed concentrate is freeze-dried to afford the purified product.

Alternatively, type $I_a$ or $I_b$ polysaccharide may be purified by the formation of Cetavlon (hexadecyltrimethyl ammonium bromide) complex. Under this procedure, the concentrated, combined active fractions are suspended in deionized water and treated with a sufficient amount of a cationic detergent such as Cetavlon to form a gel-like precipitate which in turn is dissolved in a minimum volume of 1.0 to 10% by weight, preferably 5% by weight aqueous sodium acetate. About 2 to 4 volumes of water-miscible alcohol, preferably 3 volumes of ethanol are added to precipitate the purified polysaccharide.

The purified polysaccharide, if desired, may be further purified by (1) dissolution in a buffer solution at pH about 8 to 9, preferably a borate buffer at 8.5, and (2) elution through a cellulose-packed column, for example, a Whatman's DEAE-Cellulose (DE-52) column. Active fractions are pooled, concentrated and dialzyed. The resulting retentate is freezed-dried to afford the final product.

As to types II and III, crude polysaccharides are precipitated similarly as types $I_a$ and $I_b$. However, after the initial precipitation, the crude product is suspended in an appropriate amount of an aqueous solution of an inert salt, for example, about 0.5% to 2.5% by weight aqueous sodium acetate or ammonium acetate, preferably 0.1% aqueous sodium acetate. A sufficient amount of trypsin (about 1 mg to 10 mg/100 ml of the suspension) is added and the mixture is incubated at about 34° C. to 38° C., preferably at 37° C., for about 0.5 to 2 hours or until the digestion is substantially complete. During the incubation, the pH is maintained at about 8.0 to about 8.5. Semipurified polysaccharides types II and III are subsequently obtained by the calcium chloride-ethanol precipitation as described above for types $I_a$ and $I_b$. For further purification, column chromatography with an agarose gel, for example, Sepharose® 4B, Sepharose® 6B, or Bio-gel P-300 is used. The eluate is subsequently treated with calcium chloride-ethanol to precipitate the polysaccharide which in turn is dissolved in a minimum amount of basic buffer solution of pH at about 8 to 9, preferably a borate buffer at pH 8.5. The resulting solution is eluated through a cellulose-packed column, for example, a column packed with a sufficient amount of wet Whatman's DEAE-cellulose (DE-52). Active fractions are pooled and concentrated by evaporation of the solvents followed by dialysis. The dialyzed concentrate is usually freeze-dried to afford the purified polysaccharide as a white powder.

A vaccine for humans may be prepared by incorporating an effective amount of one or more purified Group B Streptococcus type-specific polysaccharides into a suitable physiologically acceptable medium, for example, saline, water, or phosphate buffered saline.

The dosage of a monovalent vaccine and frequency of administration vary according to the age and physical condition of a patient and is up to the judgment of the clinician.

Usually the dose varies from about 25 μg to about 250 μg of the polysaccharides in about 0.2 ml to 1.0 ml sterile saline or the like. Generally, one or two subcutaneous administrations are sufficient to provide adequate protection against Group B Streptococcus infections.

In some cases, in the judgment of the clinician, it may be advantageous to prepare a polyvalent vaccine containing an effective amount of two or more selected types of Group B streptococcal type-specific polysaccharides, for example, a trivalent vaccine containing types $I_a$, II and III or a tetravalent vaccine containing types $I_a$, $I_b$, II and III. Dosage and administration of a polyvalent vaccine is substantially similar to that of a monovalent vaccine subject to the judgment of the clinician. Generally, the amount of each polysaccharides is from about 25 μg to 250 μg per dose.

Similar dosages are used in administrating a vaccine against mastitis in dairy mammals especially dairy cattle. However, an adjuvant—the role of which is to assure high immune response—is usually required. The adjuvant may be any compound or composition selected from the group consisting of aluminium hydroxide and aluminium phosphate; for example, Alhydogel®, (Superfos Export Co., Copenhagen, Denmark).

Alternatively, protection against Group B Streptococcus induced infection can be established by passive vaccination, i.e., by giving preformed antibody or homologous γ-globulin from another individual of the same or a different species. The preformed antibody or γ-globulin used for passive vaccination is usually obtained from another individual who was vaccinated actively with the vaccines of the present invention.

The following examples illustrate the present invention.

EXAMPLE 1

Fermentation of Streptococcus Group B Bacteria (Non-Dialyzed Medium)

Step A: Culture

Streptococcus Group B type $I_a$, $I_b$, II, and III were received by Merck's Rahway Stock Culture Collection (RSCC) from Dr. R. Lancefield, Rockefeller University, New York, N.Y. and were designated as Merck MB-4052, MB-4053, MB-4055 and MB-4082, respectively. The cultures were preserved as lyophilized cultures in the RSCC and have been deposited in the American Type Culture Collection (ATCC) and thereby assigned ATCC numbers 31574, 31575, 31576 and 31577, respectively. Another Type III culture, M-732 (ATCC No. 31,475), which is available on unrestricted deposit with the American Type Culture Collection, Rockville, Md., was designated as Merck MB-4316.

Step B: Inoculum Development

A lyophilized "L" tube containing one of the cultures (type $I_a$) obtained from the RSCC was suspended in 1.0 ml of BBL Fluid Thioglycollate Medium (FTM, see Table I, 1, on pg. 17) and 1.0 ml of the resulting suspension was transferred into a test tube containing 9 ml of FTM and incubated at 37° C. for 6 hours. After incubation the culture was examined microscopically and streaked on YED (see Table II, 2) plates to check for purity. Small colonies typical of Group B Streptococcus were observed on the YED plate; and numerous streptococcal chains typical of Group B Streptococcus were also observed microscopically.

Five ml of the FTM culture obtained above was used to inoculate 1 liter of inoculum medium (see Table II, 3) in a 2-liter Erlenmeyer flask. The flask was incubated stationarily for about 9 to 12 hours at 37° C. and about 4 to 12 hours at 4° C. The pH of the fermentation was adjusted periodically by the addition of 12% aqueous sodium bicarbonate. The 1 liter-fermentation utilized about 80 to 100 ml of the sodium bicarbonate solution.

Before the next inoculation, a sample was (1) applied on a YED plate to check its purity; (2) observed microsocpically; and (3) examined for precipitin reaction with Group B streptococcal antiserum (see Table II, 6). Small colonies, typical of Group B Streptococcus, were viewed on the YED; the cells were streptococcal formation when examined microscopically; and a single precipitin reaction with Group B antiserum was observed on the Ouchterlony plates.

The culture which was assured of its purity was used to inoculate a 14-liter fermentor (MA 114-New Brunswick Scientific, Edison, N.J.) containing 9 liters of inoculation medium (see Table II, 4). The batch was incubated at 37° C. with mild agitation (100 rpm) without aeration. Throughout the cultivation, samples were examined for optical density (O.D.) and pH values. The final O.D. before inoculating the production stage was about 2.0 to 5.0. The pH was maintained at about 7.0 during fermentation by the periodical addition of 10% aqueous sodium hydroxide. After the final sodium hydroxide addition, the fermentation was terminated (total time 3 hrs.). A total of 150 ml of aqueous sodium hydroxide (10%) was utilized.

Before inoculating the production fermentor, samples again were taken for purity (YED), Group B specificity (precipitin reaction on Ouchterlony), and microscopic examination. Based upon these examinations, which revealed only streptococcal forms, the production-fermentor was inoculated as described in the next step.

Step C: Production of Fermentation Broth

Approximately 10 liters of the culture obtained from Step B was used to inoculate a 250-liter fermentor (FM 250, New Brunswick Scientific) containing 175 liters of production medium (see Table II, 5). The conditions for growth were 37° C., 100 rpm agitation, and no aeration. Throughout the cultivation the pH was adjusted to 7.0 with 10% aqueous sodium hydroxide and samples were taken at 2 hr. intervals for optical density (O.D.) and pH measurements. When the pH remained constant at about 7.0 without further additions of sodium hydroxide, the fermentation was stopped.

Prior to harvesting, the culture was plated on YED, examined microscopically, checked by Gram stain (see Table II, 7), and examined for group specificity by Ouchterlony reaction. There were small colonies on the YED plate; the cells were in streptococcal formation when observed under the microscope; the Gram stain was positive; and a single precipitin reaction occurred. These results indicated that the fermentation broth was ready for harvest and inactivation. It was inactivated via addition of phenol (1% by weight).

Following substantially the same procedure as described in Example 1, but substituting for the type $I_a$ culture used therein culture type $I_b$, II, or III, there was obtained the corresponding type $I_b$, type II or type III fermentation broth.

TABLE II

| DEFINITION | | |
|---|---|---|
| 1. Fluid Thioglycollate Medium (FTM) | | |
| Fluid thioglycollate powder | 29.5 | g/liter |
| 2. YED Plates | | |
| Amberex 1003 (Amber) | 10 | gm/liter |
| Dextrose | 10 | gm/liter |
| Agar (Difco) | 20 | gm/liter |
| 3. Inoculum Medium (2-Liter Flask) | | |
| HySoy (Humko Sheffield) | 20 | gm |
| Amberex 1003 (Amber) | 10 | gm |
| NaCl | 5 | gm |
| $K_2HPO_4$ | 2.5 | gm |
| Phenol red | 10 | mg |
| The above components are dissolved in distilled water and the volume of the solution is adjusted to 900 ml. | | |
| The pH is adjusted to 7.2 and the medium is autoclaved for 25 minutes. | | |
| Glucose (25 g) in 100 ml of distilled water is autoclaved separately for 20 minutes and added aseptically to the medium. | | |
| 4. Inoculation Medium (14-Liter Fermentor) | | |
| HySoy (Humko Sheffield) | 180 | gm |
| Amberex 1003 (Amber) | 90 | gm |
| NaCl | 45 | gm |
| $K_2HPO_4$ | 22.5 | gm |
| *UCON LB 625 8% solution | 40 | ml |
| The above components are dissolved in distilled water and the volume of the solution is adjusted to 8 liters. | | |
| The pH is adjusted to 7.2 and the medium is autoclaved for 90 minutes. Glucose (225 g) in 1 liter of distilled $H_2O$ is autoclaved separately for 30 minutes and added aseptically to the medium. | | |
| 5. Production Medium (250-Liter Fermentor) | | |
| HySoy (Humko Sheffield) | 3500 | gm |
| Amberex 1003 (Amber) | 1750 | gm |
| NaCl | 875 | gm |
| $K_2HPO_4$ | 437.5 | gm |
| UCON LB 625 8% solution | 400 | ml |
| The above components are dissolved in distilled water and the volume is brought up to 165 liters. The pH is adjusted to 7.2 and the medium is autoclaved for 30 minutes. | | |
| Glucose (4375 g) in 10 liters of distilled water is autoclaved separately for 30 minutes and added aseptically to the medium. | | |
| 6. Ouchterlony Test for Group B | | |
| a. A 5 μl sample of Group B streptococcal antiserum is placed in the center well of an Ouchterlony plate (Hyland). | | |
| b. A 5 μl sample of streptococcal broth is placed in the outside well. | | |
| c. A precipitin reaction occurs if streptococcal Group B cells are present. | | |
| 7. Gram Strain | | |
| A rapid method for detecting shape and cell arrangement. The Gram strain reaction will frequently enable the investigator to narrow down the general identification to a small group. | | |

*The UCON LB 625 8% solution is pre-sterilized for 1 hour.

EXAMPLE 2

Fermentation of Type-Specific Group B Streptococcus (Dialyzed Medium)

Following substantially similar procedures as described in Example 1, steps A to C, but substituting for the media used therein the corresponding media described below in Table III, there was obtained type $I_a$, type $I_b$, type II or type III fermentation broth ready for harvesting and isolation.

TABLE III
DIALYZED MEDIA FOR DIFFERENT STAGES OF FERMENTATION

1. Inoculum Medium (2-Liter Flask)

| | |
   |---|---|
   | HySoy (Humko Sheffield) | 20 gm |
   | Amberex 1003 (Amber) | 10 gm |
   | NaCl | 5 gm |
   | $K_2HPO_4$ | 2.5 gm |
   | Phenol red | 10 mg |

HySoy and Amberex 1003 are dissolved in 50 ml of distilled water and dialyzed with 12,000 to 14,000 molecular weight cut-off. The resulting dialysate together with NaCl, $K_2HPO_4$, and phenol red are diluted with distilled water to a volume of 900 ml.
   The pH is adjusted to 7.2 and the medium is autoclaved for 25 minutes.
   Glucose (25 g) in 100 ml of distilled water is autoclaved separately for 20 minutes and added aseptically to the medium.

2. Inoculation Medium (14-Liter Fermentor)

| | |
   |---|---|
   | HySoy (Humko Sheffield) | 180 gm |
   | Amberex 1003 (Amber) | 90 gm |
   | NaCl | 45 gm |
   | $K_2HPO_4$ | 22.5 gm |
   | UCON LB 625 8% solution | 40 ml |

HySoy and Amberex 1003 were dissolved in 450 ml of distilled water and dialyzed with 12,000 to 14,000 molecular weight cut-off. The resulting dialysate together with NaCl, $K_2HPO_4$, and UCON LB 625 are diluted with distilled water to a volume of 8 liters.
   The pH is adjusted to 7.2 and the medium is autoclaved for 90 minutes. Glucose (225 g) in 1 liter of distilled $H_2O$ is autoclaved separately for 30 minutes and added aseptically to the medium.

3. Production Medium (250-Liter Fermentor)

| | |
   |---|---|
   | HySoy (Humko Sheffield) | 3500 gm |
   | Amberex 1003 (Amber) | 1750 gm |
   | NaCl | 875 gm |
   | $K_2HPO_4$ | 437.5 gm |
   | *UCON LB 625 8% solution | 400 ml |

HySoy and Amberex 1003 are dissolved in 9 liters of distilled water and dialyzed with 12,000 to 14,000 molecular weight cut-off. The resulting dialysate together with NaCl, $K_2HPO_4$ and UCON LB 625 are diluted with distilled water to a volume of 165 liters.
   The pH is adjusted to 7.2 and the medium is autoclaved for 30 minutes.
   Glucose (4375 g) in 10 liters of distilled water is autoclaved separately for 30 minutes and added aseptically to the medium

*The UCON LB 625 8% solution is pre-sterilized for 1 hour.

EXAMPLE 3

Preparation of Group B Streptococcus Polysaccharide Type $I_a$ Via Enzymatic-Digestion of the Cell Paste Step 1: Enzymatic digestion of Cell Paste The wet cell paste (105 g wet weight) obtained from the phenolized fermentation broth (Example 1) by centrifugation was suspended in 1.6 liters of 0.1 M sodium acetate with a final pH adjustment to 6.5. The resulting suspension was subsequently charged with 0.02% by weight of sodium azide as a preservative. The system underwent lysis with 4,000 azocasein units of Endopeptidase (Calgon Formulation No. 6859 113 and 005B) followed by incubation at 37° C. for 36 hr. The resulting digest (11.8 liters) was stored at 2° C. Aliquots were taken (1) for serological studies to confirm the presence of type-specific polysaccharide type $I_a$ by the Ouchterlony double immunodiffusion technique against homologus antisera (Merck, Sharp & Dohme Research Laboratories) and (2) for ethanol fractionation to determine the ethanol ranges which would precipitate the type-specific polysaccharide type $I_a$ with the aid of the serological study described in (1). It was found that 44% (vol/vol) ethanol would effectively precipitate the type $I_a$ polysaccharide.

Step 2: Preparation of Crude Type $I_a$ Polysaccharide

The digest from step 1 (1.8 liters) was treated with an aqueous solution of calcium chloride (1.1 g/ml or 0.1 M). Sufficient amount of ethanol was added at room temperature (about 20°-25° C.) until the bulk solution contained about 44% ethanol by volume. The resulting precipitates which consisted of impurities such as calcium nucleinates and cell debris were removed by centrifugation at 5,000 rpm for 10 minutes (Sorvall model RC-2B).

The supernatant was then diluted with ethanol to a concentration of 60% (vol/vol) in ethanol in order to precipitate the crude type $I_a$ polysaccharide. After sufficient time was allowed for the resulting flocculent precipitate to settle, most of the supernatant was siphoned off, and the crude product was collected by centrifugation at 5,000 rpm for 5 minutes. The crude type $I_a$ polysaccharide was suspended with 200 ml of ethanol in a Waring blender. It was subsequently filtered, washed with $1 \times 200$ ml of ethanol and $1 \times 200$ ml of acetone. After drying under vacuum in a desiccator over anhydrous calcium chloride overnight, there was obtained 2.42 g of crude type $I_a$ polysaccharide.

Step 3: Purification of Crude Type $I_a$ Polysaccharide by Molecular Sieving Chromatography The crude type $I_a$ polysaccharide (1 g) in about 10 ml of 0.5% sodium acetate (pH 6.5) containing 0.02% sodium azide (solution A) was chromatographed through a column of Bio-Gel P-300 (Bio Rad Laboratories, Richwood, Calif.) with solution A as eluant at a flow-rate of 0.4 ml/min. The elution was monitored serologically by the Ouchterlony technique. To precipitate the purified product, fractions containing the product were combined and diluted with 3 volumes of isopropyl alcohol. After standing at ambient temperature for about one hour, the supernatant was decanted, and the precipitate was triturated with 200 ml of ethanol in a Waring blender, followed by filtration and subsequent washes with ethanol (100 ml) and acetone (100 ml). The wet product was dried in vacuo over anhydrous calcium chloride to give 0.74 g of group B Streptococcus polysaccharide type $I_a$.

EXAMPLE 4

Preparation of Group B Streptococcus Polysaccharide Type $I_a$ from the Cell-Free Broth via Chemical Isolation Step 1: Preparation of Cell-Free Fermentation Broth The phenolized fermentation broth (containing 1% by weight of phenol) from Example 1 was cleared of cells by centrifugation in a Sharples Ultracentrifuge Model T-1-P.

The supernatant, 20 liters, was charged with calcium chloride dihydrate ($CaCl_2.2H_2O$) to 0.1 M in $CaCl_2$ and with denatured ethanol to 44% by volume in ethanol. The alcohol was added in 100 ml-lots per minute with adequate stirring at room temperature. The resulting suspension was allowed to stand for 4 hours and subsequently centrifuged in the Sharples Ultracentrifuge. The feeding rate of the suspension was adjusted to about 150 ml per minute to assure clarity of the effluent which was substantially free of nucleic acid and other inactive materials.

Step 2: Precipitation of Crude Type-Specific Polysaccharide

The effluent from Step 1 was charged with additional ethanol until it contained 60% by volume ethanol. A flocculent precipitate formed after standing overnight. The crude material was collected by siphoning off most of the clear supernatant followed by centrifugation at 6,000 rpm for 10 minutes at 20° C. in a Sorvall centrifuge, Model RC-5.

The resulting pellet of crude type-specific polysaccharide was suspended in 300 ml of 1% by weight aqueous sodium acetate. Usually, it required about 4 hours with mild stirring to achieve complete suspension. Insolubles were removed by centrifugation at 10,000 rpm for 15 minutes at 4° C. in a Sorvall centrifuge, Model RC-5. The supernatant (325 ml) containing the desired polysaccharide type $I_a$ was treated with 200 g of anhydrous sodium sulfate (86% saturation) with adequate agitation. Since the salted-out material tended to rise to the surface, the entire system was degassed under mild vacuum in order to facilitate the precipitation. After standing overnight at 4° C., the precipitated crude polysaccharide type $I_a$ was collected by centrifugation in the usual manner as described above.

Step 3: Isolation of Group B Streptococcus polysaccharide Type $I_a$ by Sepharose 6B Chromatography The salted-out material from step 2 was extracted with 30 ml of 1% aqueous sodium acetate to give a viscous solution. The remaining turbidity was removed by centrifugation at 15,000 rpm for 20 minutes at 4° C. The almost clear supernatant (ca. 30 ml) was applied to a Sepharose 6B column with a bed volume of $5.6 \times 90$ cm preequilibrated with the eluant (1% sodium acetate containing 0.02% sodium azide as a preservative, with a pH of 7.3). Fractions (12.5 ml) were collected for maximal flow rate of ca. 1 ml per minute.

The elution was monitored by (1) refractive index changes (Waters Associates), and (2) by the Ouchterlony double immunodiffusion technique for serological activity. It was found that peak serological activity coincided with a refractive index peak. The serologically active fractions were pooled and was reduced in volume to ca. 30 ml in a hollow fiber device, No. 80, (100 ml beaker, Bio Rad Laboratories, Richmond Cal.). The ionic strength of the pooled fractions was reduced to less than 0.25% by flushing with apyrogenic water. By backflushing the device with about 70 ml of water, the combined active fractions were efficiently recovered with a total volume of about 100 ml and were used directly in the next step.

Step 4: Further Purification of Group B Streptococcus polysaccharide type $I_a$ via Cetavlon Complex Formation The pooled active fractions (100 ml) from Step 3 was charged with 300 mg of Cetavlon. A glassy gel-like precipitate was formed and was collected at once by centrifugation at 10,000 rpm for 10 min. at 4° C. (Sorvall, Model RC-5). To test for the completeness of the complex formation and to assure that the initially existing ionic strength of foreign ions was not too high, the supernatant was dialyzed overnight against a 1% by weight aqueous solution (500 ml) of Cetavlon. The completeness of the complex formation was indicated by the lack of further complex formation, i.e., the supernatant stayed clear after the test.

The complex was suspended in 20 ml of 5% sodium acetate to give a clear, slightly viscous, colorless solution. The desired polysaccharide type $I_a$ was precipitated with 3 volumes of ethanol. A heavy, flocculent precipitate resulted and the supernatant decanted. The precipitate was washed with 250 ml of ethanol to remove any sodium acetate remaining in the precipitate. It was further washed with acetone, and air-dried.

The resulting powder was transferred into a 100 ml round-bottom flask and dissolved in 20 ml of 0.02% sodium acetate. The clear solution was dialyzed against 1 liter of water and the dialyzed concentrate was freeze-dried to afford 205 mg of purified Group B Streptococcus polysaccharide, type $I_a$.

Following substantially the same procedure of Example 4 but substituting for the type $I_a$ specific antiserum used therein for the Ouchterlony double immunodiffusion technique for serological activity, the type $I_b$ specific antiserum, there was obtained 5–10 mg/liter of broth of purified Group B Streptococcus type $I_b$ polysaccharide.

EXAMPLE 5

Preparation of Purified Group B Streptococcus Polysaccharide, Type $I_b$

Step 1: Preparation of Cell-Free Fermentation Broth

At the end of the fermentation cycle, the broth was phenolized to contain 1% by volume of phenol. Cells were subsequently removed by centrifugation in a Sharples supercentrifuge, Model T-1-P, and the supernatant was stored at 4° C. overnight.

Step 2: Precipitation of the crude Group B Streptococcus Polysaccharide, Type $I_b$ The cold supernatant (10 l) from step 1 was charged with calcium chloride dihydrate until its concentration reached 0.1 M. The temperature of the supernatant rose to about 15° C. due to the exothermic solubilization of the salt. Without cooling, a sufficient amount of ethanol was added with stirring until the resulting mixture contained 60% by volume of ethanol and the precipitation of impurities began. After standing at room temperature for 24 hours, the supernatant was decanted, and the precipitate was collected at 20° C. by centrifugation for 10 min. at 5,000 rpm. The wet precipitate (280 ml) was suspended in 5 volumes (1400 ml) of 0.5% by weight aqueous sodium acetate followed by treatment with calcium chloride and ethanol to give a final mixture containing 0.1 mole/liter of calcium chloride and 44% by volume ethanol.

The ethanol addition was carried out at a rate of 10 ml/min. with adequate stirring. After standing for 2 hours at ambient temperature, the precipitate (calcium nucleinates) was discarded by centrifugation, and the ethanol content of the clear supernatant was adjusted to 60% by volume with additional amount of ethanol. The resulting suspension was allowed to stand overnight to precipitate most of the desired polysaccharide, type $I_b$. Upon centrifugation, a wet pellet of crude polysaccharide was collected.

Step 3: Precipitation of semi-purified Polysaccharide with Ammonium Sulfate

The pellets were suspended in 300 ml of 1% aqueous sodium acetate. Insolubles were removed by centrifugation at 10,000 rpm for 15 minutes at 4° C. in a Sorvall centrifuge, model RC-5.

The volume of the supernatant was noted and the extract partially saturated (85% saturation) with anhydrous ammonium sulfate to salt out the polysaccharide. The suspension was degased in a desicator under vacuum followed by standing at 4° C. overnight. The precipitated polysaccharide was collected by centrifugation as described above.

Step 4: Preparation of Purified Polysaccharide type $I_b$ by Chromatography

The precipitates from Step 3 were extracted with 20 ml of 1% aqueous sodium acetate with insolubles removed by centrifugation at 15,000 rpm for 10 minutes and at 4° C. The clear supernatant (10 ml) was applied to a column of Sepharose 6B (2.6×90 cm) and developed with 1% aqueous sodium acetate containing 0.02% sodium azide as preservative. Fractions of 12 ml each were collected (flow rate ca. 3 fractions/min.). The elution was monitored for type $I_b$ polysaccharide by the Ouchterlony double immunodiffusion technique. The serologically active fractions were pooled and concentrated to ca. 20 ml by evaporation. The concentrate was dialyzed for 4 hours against 1 liter of distilled water followed by 18 hours against 2 liters of 0.02% by weight aqueous sodium acetate 4° C. The dialyzed concentrate was freeze-dried to afford 235 mg. of purified group B Streptococcus polysaccharide, type $I_b$.

EXAMPLE 6

Preparation of Group B Streptococcus Polysaccharide Type $I_a$

Employing substantially similar procedures as described in Example 5, Steps 1-4, but using type $I_a$ broth and substituting for the antiserum used therein for monitoring polysaccharide type $I_b$, the appropriate amount of polysaccharide type $I_a$-specific antiserum for detecting the type $I_a$ serologically active fractions, there was prepared 25 mg of purified Group B Streptococcus polysaccharide, type $I_a$.

EXAMPLE 7

Preparation of Group B Streptococcus Type III Polysaccharide

Step 1: Isolation of Crude Group B Streptococcus Type III Polysaccharide

Employing essentially the same procedures of Example 4, Steps 1 and 2, there was obtained the crude type III polysaccharide precipitate from the phenolized fermentation broth of Example 1. It was suspended in 200 ml of 1% by weight aqueous sodium acetate (pH 8.5) to give a slightly cloudy solution. Five miligrams of highly purified trypsin (Wortington Co., Freehold, N.J.) were added followed by incubation at 37° C. for 1 hr. pH value of the solution was maintained at 8.0 to 8.5 during the incubation period. The resulting digest was cooled to about 0°-10° C. Precalculated amount of solid calcium chloride and ethanol were added so as to make the final concentration of the solution 0.1 M in calcium chloride and 61% (v/v) in ethanol. A suspension resulted. It was allowed to stand overnight for complete precipitation. After the clear supernatant was decanted, the precipitates were collected by centrifugation (5 minutes at 5,000 rpm, 20° C.).

Step 2: Purification of Group B Streptococcus Polysaccharide Type III

The crude precipitates obtained in step 1 was extracted with 10 ml of 1% aqueous sodium acetate. After centrifugation, the clear supernatant was applied to a 2.6×90 cm Sepharose 6B column (Pharmacia Co., Piscataway, N.J.) and was eluted with 1% by weight aqueous sodium acetate containing 0.02% by weight of sodium azide, a preservative agent. Twelve milimeter fractions were collected at a flow rate of 3 fractions per hour. The elution was followed by Ouchterlony double immunodiffusion techniques against type III specific rabbit antiserum and serologically active fractions were identified and pooled. It was diluted with four volumes of ethanol to precipitate semi-purified type III polysaccharide which in turn was centrifuged upon completion of the precipitation. The pellet was successively washed with ethanol and acetone. It was dried under vacuum in the presence of anhydrous calcium chloride to afford 65 mg of semi-purified product.

Step 3: Final Purification of Group B Streptococcus Polysaccharide Type III by DEAE-Cellulose Column Chromatography The semi-purified polysaccharide from Step 2 was dissolved in 100 ml of 0.05 M borate buffer (pH 8.5) and applied to a 1.0 cm×30 cm column packed with 20 g of wet Whatman's DEAE-cellulose (DE-52) preequilibrated with 0.05 M sodium borate at pH 8.5. Under these conditions the type III polysaccharide will associate with the cellulose, while remaining impurities will wash through. For this reason, the DEAE-cellulose column was washed with 200 ml of 0.05 M sodium borate (pH 8.5) to remove most of the impurities. Subsequently, the type III polysaccharide associated with the cellulose was eluted with 0.2 M aqueous sodium chloride in 0.05 M sodium borate buffer at pH 8.5. Fractions of 5 ml were collected and the emergence of the type III polysaccharide was monitored by the Ouchterlony double immunodiffusion technique against type III-specific antiserum. Active fractions were pooled and were concentrated by evaporation to about 20 ml and the concentrate was dialyzed for 24 hours against 0.02% by weight sodium acetate at 4° C. The dialyzed concentrate was freeze-dried to give 35 mg of purified Group B Streptocuccus polysaccharide type III.

Following substantially the same procedure as described in Example 7, but substituting for the type III-specific antiserum used therein for monitoring polysaccharide type III, the type II-specific antiserum for detecting the serologically active fractions, there was prepared 230 mg of purified Group B Streptococcus polysaccharide, type II.

EXAMPLE 8

Preparation of Group B Streptococcus Type III Polysaccharide From Cell-Free Broth Obtained From Fermentation in Dialyzed Medium Following substantially similar procedures as described in Example 7, Steps 1 to 3, but substituting for the phenolized fermentation broth used therein, the fermentation broth obtained from Example 2, there was prepared 300 mg of purified Group B Streptococcus polysaccharide type III.

EXAMPLE 9

Vaccine—Dosage Form

One tenth gram of the purified polysaccharide type III was suspended in 500 ml of pyrogen-free distilled water. The suspension was sterile filtered and packed in vials, 5 ml per vial for 10 doses or 100 μg per dose. The vaccine so obtained may be administered subcutaneously or intramuscularly to expecting mothers or women of child bearing age.

EXAMPLE 10

Vaccine—Dosage Form

Two tenth grams each of the purified polysaccharide types II and III were added with sufficient stirring and under aseptic conditions to 1.5 liters of pyrogen-free saline (0.85% by weight). After the addition, the mixture was stirred at room temperature for an additional 2 to 5 minutes, and sterile filtered. The clear filtrate was distributed into 10 ml vials which were either sealed or tightly stopped under aseptic conditions. Each vial contained 5 ml of the filtered vaccine corresponding to 10 doses (about 60 to 65 μg/dose) for injection.

EXAMPLE 11

Polyvalent Vaccine

A polyvalent vaccine was prepared by adding under aseptic conditions at room temperature the following amounts of capsular polysaccharide to 4 liters of pyrogen-free saline (0.85%). The polysaccharides were added individually at 15 second intervals while stirring continuously in a blender. After the addition was complete, the stirring was continued for another 2 to 3 minutes.

| Type | Amount (gram) |
|---|---|
| $I_a$ | 1.6005 |
| $I_b$ | 0.8210 |
| II | 0.6005 |
| III | 1.2400 |
| | 4.2620 |

The mixture was subsequently sterile filtered and packaged in vials, 5 ml (10 doses) per vial, i.e., about 75 μg (type II) to 200 μg (type $I_a$) per dose.

In Examples 12–15, the following reagents are used:

Acetone, Baker Analyzed
Ammonium Sulfate, Fisher Scientific Co. or Schwarz-/Mann
Boric Acid, Merck & Co.
Calcium Chloride, Dihydrate, Baker Analyzed
Cetavlon (Hexadecyltrimethyl-ammonium Bromide), Eastman Kodak—a cationic detergent
DEAE-Cellulose (DE-52), Whatman Ltd.
Ethanol, Denatured (toluene), Merck & Co.
Ethanol, Denatured, 2BA, Type T, Merck & Co.
Ethanol, 200 Proof, U.S. Industrial Chemicals Co.
Glacial Acetic Acid, Merck & Co.
Sepharose 6B, Pharmacia
Sodium Acetate, Anhydrous, Mallinckrodt
Sodium Chloride, Baker Analyzed
Sodium Hydroxide, 50% Solution, Baker Analyzed
Trypsin, Worthington, 238 units/mg.

Reagents are prepared with triply distilled water. Likewise all containers are rinsed in this water.

EXAMPLE 12

Release Protocol For Group B Streptococcus Type Ia Polysaccharide, Product 11059-113

Step 1—Isolation of First Crude Product

Sixty (60) liters of whole, phenolized broth were charged with 885 gm of calcium chloride, dihydrate to 0.1 M. Ethanol (denatured) was then added to the 44% vol/vol level. The suspension was allowed to stand for maximal settling of the cells and other insolubles (about 48 hours). The clear supernatant was then transferred into another fractionation vat, with a recovery of 73 liters. Of this volume, 41 liters represent the aqueous phase. On this basis 29 liters of ethanol (denatured) were added to raise the ethanol level to 60%. Again, the suspension was allowed to stand for maximal settling of the precipitate which contains the desired polysaccharide. The clear supernatant was then pumped off and the precipitate collected by centrifugation (Beckman, Model J-21C, in 500 ml cups, for 15 minutes at 6,000 RPM and at 20° C.).

Step 2—Extraction of the Polysaccharide

The rubbery pellets were suspended with the aid of a blender in 1800 ml of 1% sodium acetate with pH adjustment to 8.5 (using 2 N sodium hydroxide). The suspension was then cleared by centrifugation (as in Step 1, except for 30 minutes at 8,000 RPM). There was a firm pellet, overlaid, however, by a creamy paste, which made it necessary to aspirate off the clear supernatant as decantating was not possible. The total volume was 1,240 ml extract.

Step 3—Removal of Proteinaceous Materials with Trypsin

The extract from Step 2 was charged with 30 mg trypsin and incubated at 37° C. for 90 minutes. The pH was monitored for the range 8.2–8.6 during the incubation period. The digest was then immediately placed in an ice-bath.

Step 4—Ammonium Sulfate Precipitation of the Polysaccharide

While in an ice-bath the digest was charged with ammonium sulfate (750 gm) to 86% saturation. The resulting suspension was allowed to stand at 4° C. overnight to precipitate the polysaccharide. The clear supernatant was removed by aspiration and the salted out material was collected by centrifugation as described in Step 1.

Step 5—Chromatography on DEAE-Cellulose

The ammonium sulfate precipitate from Step 4 was dissolved in 200 ml 1% sodium acetate and exhaustively dialyzed for 48 hours (2×12 hours against 10 liters distilled water, followed by 24 hours against 10 liters of 0.05 M borate buffer, pH 8.5). A light turbidity in the retentate was cleared by centrifugation (Sorvall, Model RC-5, in 50 ml cups, at 15,000 RPM for 20 minutes at 4° C.). The clear supernatant fluid was then applied to a column of DEAE-Cellulose, equilibrated with sodium borate (0.05 M, pH 8.5), (dimensions of 5.0×30 cm). The column was then washed with 700 ml borate buffer. Sodium chloride (0.3 M) in borate buffer, 800 ml, was then applied to a column to mobilize the adhering polysaccharide. One hundred milliliter (100 ml) fractions were collected and separately assayed serologically for their polysaccharide content. Active fractions (2–8) were pooled and the pool treated with 1.5 volumes of ethanol (denatured) to precipitate the polysaccharide which was recovered after removal of the clear supernatant and by centrifugation (as per Step 1). Pellet volume was estimated as 10 cm$^3$.

Step 6—Recovery of the Polysaccharide as a Cetavlon Complex

The precipitate from Step 5 was resuspended in 300 ml triply distilled water to give a clear solution. One hundred milliliters (100 ml) of a 3% solution of Cetavlon in water was then added with stirring. The polysaccharide aggregated into a single lamp allowing its easy removal.

Step 7—Recovery of Product Intermediate 11059-101

The complex from Step 6 was solubilized in 200 ml 15% sodium acetate, at pH 8.0 at 4° C. It took several hours to achieve complete solubilization. The solution was finally charged with two volumes of ethanol (denatured) to precipitate the polysaccharide as its sodium salt. The precipitate was collected, after removal of the clear supernatant, by centrifugation, as per Step 1. The pellet was triturated with about 100 ml ethanol (denatured) in a blender then collected on a small sintered glass funnel (15 ml, M), washed thereon with 50 ml ethanol and 50 ml acetone, followed by drying in a vacuum desiccator. The product intermediate was called 11059-101, (yield 805 mg).

Step 8—Molecular Sieving on Sepharose 6B and Final Product Recovery

Two hundred milligrams (200 mg) of 11059-101 were dissolved in 12 ml column buffer (1% sodium acetate) and the solution applied to a column of Sepharose 6B (2.6×90 cm) equilibrated with 1% sodium acetate. Fractions of 12.5 ml were collected and active fractions were identified by the Ouchterlony double immunodiffusion method, using a type specific antiserum. Active fractions (14–29) were pooled. The operation was then repeated with a second 200 mg portion of 11059-101. The 2 pools were combined and concentrated in a Bio Rad No. 80 hollow fiber device to 100 ml. The concentrate was treated with 2 volumes of ethanol (200 proof) to precipitate the polysaccharide. The precipitate was allowed to settle out and recovered, after removal of the supernatant and by centrifugation as per Step 1. The precipitate was then triturated with 50 ml ethanol (200 proof) in a blender and was collected on a small sintered glass funnel (15 ml, M), washed thereon with 50 ml ethanol (200 proof) and 50 ml acetone, followed by drying in a vacuum desiccator to constant weight. Final product: 11059-113 (yield 300 mg).

EXAMPLE 13

Release Protocol for Group B Streptococcus Type Ib Polysaccharide, Product 11059-186

Step 1—Preparation of Cell-Free Fermentation Broth

Type Ib broth, phenolized to 1% at termination of the fermentation cycle, was cleared of cells by centrifugation in a Sharples ultracentrifuge, Model T-1P.

Step 2—Ultrafiltration/Diafiltration of Cell-Free Broth

Sixty liters (60 liters) of the cell-free supernatant were pumped through an ultrafiltration hollow fiber device (Amicon, Model DC-2; molecular weight cut-off of fibers of 50,000 daltons) to a final volume of 11.29 liters.

Step 3—Isolation of First Crude Product

The concentrate was charged with calcium chloride to 0.1 M and subsequently with ethanol (denatured 2 BA, T type) to 30% by volume. The resulting suspension was centrifuged in a Sharples centrifuge to obtain a clear supernatant (15.13 liters). The ethanol level was then raised to 61% by the addition of 12.06 liters of ethanol (denatured). The resulting precipitate was obtained by allowing it to settle out, removing of most of the clear supernatant, and finally by centrifugation (Beckman, Model J-21C, 50 ml-cups, 15 minutes, 20° C., 6,000 RPM).

Step 4—Isolation of Second Crude Product

The first crude was suspended in 1,800 ml of 3% sodium acetate and full solubilization assured by stirring the suspension vigorously overnight at 4° C. A serological probe performed on a small aliquot of the suspension indicated that the desired polysaccharide is fractionable with ethanol in the 40–60% range. The total volume of the suspension was 1,980 ml. The suspension was accordingly charged with 1,220 ml ethanol (denatured) to the 40% level and the alcoholic suspension cleared by centrifugation in the Beckman as described in Step 3. A considerable amount of insoluble materials were removed at 40% ethanol. The clear supernatant was then charged with additional (1,650 ml) ethanol (denatured) to 60%, and the resulting suspension was allowed to stand for 48 hours to let the insolubles settle out. The insolubles (second crude) were then recovered by removal of most of the supernatant and by centrifugation as already described.

Step 5—Isolation of the Polysaccharide as a Cetavlon Complex

The wet pellets, ca. 40 cc in volume, were dissolved in 250 ml water to give a clear, but pigmented solution. The solution was then dialyzed for 24 hours to remove traces of sodium acetate. The retentate was then charged with 100 ml of a 5% solution of Cetavlon in water. The resulting suspension was let stand at 4° C. for 18–20 hours to allow the complexing to go to completion. A small aliquot of the suspension was cleared by centrifugation and the supernatant checked for completion of complexing by adding more Cetavlon to the clear supernatant. There was no further precipitate. The Cetavlon-polysaccharide complex was then collected by centrifugation in a Sorval centrifuge, Model RC-5, in 50 ml cups, for 10 minutes at 15,000 RPM and at 4° C. The pellet was not entirely firm, but with a consistency of molasses allowed of the quick decantation of the clear supernatant.

Step 6—Recovery of the Third Crude Product

The Cetavlon complex was extracted with 200 ml of a 15% solution of sodium acetate at pH 8.0 and the cleared extract (by centrifugation) charged with 2 volumes of ethanol (denatured). A gum formed which settled out overnight, allowing the total decantation of the alcoholic supernatant.

Step 7—De-Ionization of the Third Crude Product

The third crude was taken up in 200 ml 0.05 M borate buffer, pH 8.5 and ultrafiltered in an Amicon stirred cell (200 ml capacity, equipped with a 30,000 dalton cut-off membrane). To remove traces of sodium acetate the volume was reduced to 50 ml then increased to 200 ml with borate buffer, followed by reduction to 50 ml.

Step 8—DEAE-Cellulose Fractionation of the Third Crude Product

The retentate from Step 7 was applied to a column of DEAE-cellulose (5.0×30 cm), equilibrated with 0.5 M borate buffer, pH 8.5. The column was washed with 700 ml borate buffer. The wash did not give a precipitate with 1.5 volumes ethanol, nor did it contain any trace of serologically active material in a test with type specific antiserum (Ib) by the Ouchterlony double immunodiffusion method. The column was then washed with 0.25 M sodium chloride in borate buffer and 100 ml fractions collected. Fractions containing serologically active material (No. 4–10) were pooled, and the polysaccharide was precipitated with 1.5 volumes of ethanol (denatured). After the precipitate had settled out, most of the supernatant was removed by aspiration and the precipitate was finally collected by centrifugation (Sorvall, as described in Step 5). This material was designated the Fourth Crude.

Step 9—Trypsin Digestion of Fourth Crude Product to Obtain the Fifth Crude Product The precipitate from Step 8 was dissolved in 150 of a solution of 3% sodium acetate and the pH adjusted down to 8.5. A blender was used to speed up the dispersion of the material. Trypsin was added (20 mg; 238 units/mg), and the system incubated for 90 minutes at 37° C. The pH was monitored from time to time, but found unchanged throughout the incubation cycle. The digest was then charged with 1.5 volumes of ethanol (denatured) and the precipitate collected by centrifugation in a 500 ml cup (Beckman centrifuge). The pellet was triturated in a small blender with absolute ethanol, collected on a small sintered glass funnel (15 ml, M), washed thereon with 50 ml absolute ethanol and 50 ml of acetone and finally dried in a vacuum desiccator overnight. A white powder was obtained, product intermediate (Fifth Crude) 11059-185, with a yield of 741 mg.

Step 10—Purificatin with Ammonium Sulfate

Product intermediate 11059-185, as shown by Sepharose 6B profiling, still carries a considerable amount of contaminant, masking in part the type polysaccharide. It was therefore decided to precipitate the desired polysaccharide with ammonium sulfate, at 86% saturation. The lot of the product intermediate was dissolved in 100 ml triply distilled water, and the solution was charged with enzyme grade ammonium sulfate (61 gm). The resulting suspension was let stand in the cold for 2 hours, and the precipitate was then recovered by centrifugation (Sorvall, 15,000 RPM, 50 ml cups, for 15 minutes at 2° C.).

Step 11—Molecular Sieving of Ammonium Sulfate Precipitate

The pellets from the previous step were dissolved in 12 ml eluant (1% sodium acetate, pH 7.5). The clear solution, with a pale-yellow pigmentation, was then applied to a column of Sepharose 6B, equilibrated with 1% sodium acetate, pH 7.5, (dimensions of 2.6×90 cm). Fractions of 12.5 ml were collected, and their polysaccharide content monitored serologically by Ouchterlony double immunodiffusion technique. Active fractions were pooled.

Step 12—Recovery of Final Product, 11059-186

The pool (213 ml) from Step 11 was diafiltered and concentrated to 20 ml in a suitable Amicon cell, equipped with a 30,000 M. W. cut-off membrane. The concentrate was then charged with 2 volumes of absolute ethanol to precipitate the polysaccharide. This was separated by centrifugation, discarding the supernatant. The pellet was triturated in a small blender with absolute ethanol and the hardened particles collected on a sintered glass funnel. The polysaccharide was washed thereon with 50 ml absolute ethanol and 50 ml acetone and dried in a vacuum desiccator for 24 hours to constant weight. Final Product: 11059-186 (yield 189 mg).

EXAMPLE 14

Release Protocol for Group B Streptococcus Type II Polysaccharide, Product 11059-176

Step 1—Isolation of First Crude Product

Eighty (80) liters of whole, phenolized broth were charged with 1,170 gm of calcium chloride, dihydrate, to 0.1 M. Ethanol (denatured) was then added to the 40% level (vol/vol). The suspension was allowed to stand for maximal setting of the cells and other insoluble materials (about 48 hours). The clear supernatant was then pumped over into another fractionation vat, with a recovery of 94 liters. The aqueous phase in this system was calculated as 56.4 liters. On this basis, additional 47 liters of ethanol (denatured) were run in with stirring, to an ethanol level of 60%. Again, the suspension was allowed to stand for maximal settling of the precipitate which contains the desired polysaccharide. The clear supernatant was then aspirated off with the aid of a pump, and the precipitate collected by centrifugation (Beckman, Model J-21C, in 500 ml cups, for 15 min. at 6,000 RPM and at 20° C.).

Step 2—Isolation of Second Crude Product

The precipitate from Step 1 was resuspended in 1% sodium acetate (3,000 ml), giving a final volume of 3,340 ml and the suspension charged with calcium chloride to 0.1 M. Based on a serological probe it could be demonstrated that the desired polysaccharide can be fractionated with ethanol in the range of 38–59%. Accordingly, the suspension was charged with 2,050 ml of ethanol (denatured) to the 38% level. The suspension was cleared by centrifugation, as per above, Step 1. Of the total supernatant recovered (4,850 ml) 3,010 ml constitute the aqueous phase. The supernatant was then charged with ethanol (denatured) (2,470 ml) to 59%. A flocculent precipitate developed and settled out readily. It was allowed to settle out and the clear supernatant was removed by aspiration. The precipitate was then collected by centrifugation, as already described.

Step 3—Removal of Proteinaceous Materials with Trypsin

The slightly pigmented pellet from Step 2 was dissolved in 500 ml 0.05 M sodium borate, pH 8.5 and the solution was charged with 20 mg trypsin (4,760 unit). The system was incubated at 37° C. for 90 minutes.

Step 4—Chromatography on DEAE-Cellulose

The trypsin digest from Step 3 was applied to a column of DEAE-Cellulose (DE-52, Whatman), equilibrated in 0.05 M sodium borate at pH 8.5, (dimension: 5×30 cm). The column was then washed with 700 ml borate buffer. The column was then treated with 800 ml of eluant, containing 0.3 M sodium chloride in borate buffer. Effluent fractions (100 ml) were collected and separately assayed serologically for their polysaccharide content, and for precipitability with 1.5 volumes ethanol. Fraction No. 1 did not give a precipitate, Nos. 4 and 5 had the highest amounts of precipitate, and No. 8 gave only a weak precipitate. Fractions No. 2–7 were pooled and the pool charged with 1.5 volumes of ethanol (denatured) to precipitate the polysaccharide.

Step 5—Isolation of Third Crude Product

The precipitate from Step 4 was taken up in 300 ml distilled water, diafiltered to 100 ml, and the process repeated twice more, in each case with replenishing the volume to 300 ml with distilled water. The final retentate of 100 ml was charged with sodium acetate to 1% and the polysaccharide precipitated with 1.5 volumes of ethanol (denatured). The precipitate was collected by allowing it to sediment and by decantating of the clear supernatant. The precipitate was then triturated in a blender with ethanol (denatured) and collected on a small sintered glass funnel (15 ml, M), washed thereon with 50 ml ethanol (denatured) and with 50 ml acetone and dried in a vacuum desiccator. Product intermediate: 11059-160 (yield of 2.654 gm).

Step 6—Cetavlon Complexing of the Polysaccharide

The lot of product 11059-160 was dissolved in 265 ml triply distilled water to give clear, slightly pigmented solution. The solution was then placed in an ice-bath and while stirred, a solution of 2.65 gm Cetavlon in 50 ml of water was added. The resulting suspension was kept at 0° C. for 60 minutes. The Cetavlon-polysaccharide complex was then recovered by centrifugation (Sorvall RC-5, in 50 ml cups, at 2° C., 15,000 RPM, for 40 minutes). The supernatant was carefully decanted from a semi-liquid, viscous pellet. The liquid complex was immediately solubilized in 15% sodium acetate (150 ml) at pH 8.4. The clear solution was then charged with ethanol (denatured) to the 60% level, and the precipitate which formed was allowed to settle out. After total decantation of the supernatant, the precipitate was triturated with ethanol in a blender and collected on a small sintered glass funnel (15 ml, M). It was washed thereon with 50 ml of ethanol (denatured), and with 50 ml acetone, followed by drying in a vacuum desiccator. Product Intermediate: 11059-174 (yield 710 mg).

Step 7—Molecular Sieving on Sepharose 6B and Recovery of Final Product

Four hundred (400) milligrams of product intermediate 11059-174 were dissolved in 12 ml 1% sodium acetate (eluant) and applied to a column of Sepharose 6B (2.6×90 cm; equilibrated with 1% sodium acetate). Fractions of 12.5 ml were collected and active fractions were identified by the Ouchterlony method, using type-specific antiserum. Fractions 12–30 were pooled and the pool was reduced in volume to 150 ml in an Amicon stirred cell using YM 30 membrane (having a molecular weight cut-off of 30,000 daltons). The concentrate was then transferred into a 600-ml beaker and precipitated with two volumes of ethanol (200 proof). The precipitated polysaccharide was allowed o settle out and the clear supernatant removed by decantating. The sticky settlement was triturated in a blender with ethanol and collected on a small sintered glass funnel (15 ml, M) and washed thereon with 50 ml ethanol and 50 ml acetone. It was then dried in a vacuum desiccator to constant weight. Final Product 11059-176 (yield of 285 mg).

EXAMPLE 15

Release Protocol for Group B Streptococcus Type III Polysaccharide, Product 11059-179

Step 1—Preparation of Cell-Free Fermentation Broth

Type III broth, phenolized to 1% at termination of the fermentation cycle, was cleared of cells by centrifugation in a Sharples ultracentrifuge, model T-1P.

Step 2—Ultrafiltration/Diafiltration of Cell-Free Broth

Two hundred (200) liters of the cell-free supernatant from Step 1 were pumped through an ultrafiltration hollow fiber device (Amicon unit, Model DC-2, molecular weight cut-off of 50,000 daltons) to a final volume of 14.9 liters.

Step 3—Isolation of First Crude Product

The concentrate from Step 2 (14.9 liters) was charged with calcium chloride to 0.1 M and the pH adjusted to 8.2 with 2 N NaOH. It was then charged with 4.95 liters, ethanol (denatured, 2BA T-Type), to 30% by volume. The resulting suspension was centrifuged in a Sharpless centrifuge to obtain a clear supernatant (19.0 liters). The aqueous phase of the supernatant was calculated at 14.25 liters. On this basis, the supernatant was charged with additional 21.7 liters ethanol (denatured) to a level of 65%. The resulting suspension was let stand for several days, during which time the desired polysaccharide settled out. The bulk of the clear supernatant was pumped off and the precipitate was collected by centrifugation in 500-ml cups (Beckman, Model J-21C, at 6,000 RPM, 20° C., for 15 minutes). The pellet was triturated in a blender with ethanol (denatured) and collected on a sintered glass funnel (50 ml, M), washed thereon with 50 ml ethanol (denatured) and with 50 ml acetone, followed by drying in a vacuum desiccator overnight. Product 11059-167 (yield 7.22 gm).

Step 4—Cetavlon Complexing and Recovery of Second Crude Product

Seven (7) grams of product intermediate 11059-167 were dissolved in 700 ml ice-cold water and after stirring for one hour the suspension was cleared by centrifugation. The clear supernatant was then charged with 100 ml of a 7.5% solution of Cetavlon and the resulting suspension allowed to stand at 4° C. overnight. The insoluble Cetavlon-polysaccharide complex was collected by centrifugation (Sorvall RC-5, in 50-ml cups, at 15,000 RPM, 4° C. for 10 min). The supernatant was decanted from a semi-soft, honey-like pellet. The complex was suspended for extraction in 500 ml 15% sodium acetate (no pH adjustment was needed, since it was noted at 8.2). The suspension was stirred for several hours in the cold to assure maximal solubilization. The centrifugation step was repeated to remove some insoluble, pigmented material. The extracted polysaccharide was precipitated from the extract by the addition of ethanol (denatured) to the 61% level. A sticky gum settled out, allowing the supernatant to be decanted totally.

Step 5—Removal of Protein by Trypsin Digestion and Recovery of the Third Crude Product The gum from Step 4 was dissolved in 100 ml of a 3% solution of sodium acetate, with adjustment of the pH to 8.4. The solution was transferred into a 500-ml centrifuge cup, and charged with 20 mg trypsin. The system was then incubated at 37° C. for 90 min. with occasional monitoring of the pH. No further pH adjustments needed to be made. At the conclusion of the digest cycle, the polysaccharide was recovered by the addition of 2 volumes of ethanol (denatured). The precipitate was collected by centrifugation (Beckman, Model J21C, at 6,000 RPM, at 20° C. and for 10 minutes). The pellet was triturated with ethanol (denatured) in a blender, collected on a small sintered glass funnel (15 ml, M) washed thereon with 50 ml ethanol (denatured) and 50 ml acetone, followed by drying in a vacuum desiccator overnight. Product Intermediate 11059-170 (yield 1,357 mg).

Step 6—Molecular Sieving of Product Intermediate 11059-170

Four hundred (400) milligrams of 11059-170 were dissolved in 12 ml eluant (1% sodium acetate, pH 7.5). The clear solution was then applied to a column of Sepharose 6B, equilibrated with 1% sodium acetate, pH 7.5, (dimensions of 2.6×90 cm). Fractions of 12.5 ml were collected and their polysaccharide content monitored serologically by the Ouchterlony double immunodiffusion technique. Active fractions (15-32) were pooled and concentrated to ca. 70 ml (Amicon stirred cell, equipped with a 30,000 M. W. cut-off membrane).

Step 7—Recovery of Final Product

The concentrated pool from Step 6 was then charged with two volumes of 200 proof ethanol. The gummy precipitate which settled out was removed from the precipitation flask and triturated with absolute ethanol in a blender, collected on a small sintered glass funnel (15 ml, M), washed thereon with 50 ml absolute ethanol and 50 ml acetone, followed by drying in a vacuum desiccator to constant weight. Product 11059-179 (yield of 272 mg).

What is claimed is:

1. A process for the preparation of an antigenic type-specific polysaccharide of Group B Streptococcus comprising
   (a) growing the Group B Streptococcus bacteria types $I_a$, $I_b$, II, or III in a high glucose, soy bean and yeast extract fermentation medium;
   (b) separating the cell paste from the liquid medium;
   (c) treating the liquid medium from step (b) with a strong ionic salt and a water-miscible lower alkanol to precipitate impurities or alternatively digesting the cell paste with an enzyme to obtain a liquid extract;
   (d) precipitating the crude polysaccharide from the treated liquid medium, or if desired, the liquid extract from digested cell paste with a sufficient amount of water-miscible lower alkanol;
   (e) suspending the crude polysaccharide of step (d) in deionized water and adding thereto sufficient cationic detergent to precipitate the polysaccharide;
   (f) redissolving the polysaccharide in 15% (wt/wt) sodium acetate aqueous solution; and
   (g) precipitating the semi-purified polysaccharide from the solution with alcohol and, optionally, digesting the resulting precipitate with a proteolytic enzyme, followed by precipitating the enzyme-treated polysaccharide with a sufficient amount of water-miscible alkanol.

2. A process of claim 1, wherein the cationic detergent is hexadecyltrimethylammonium bromide.

3. A process of claim 1 wherein steps (c) and (d) are:
   (c) treating the liquid medium from step b with a strong ionic salt and a water-miscible lower alkanol to precipitate impurities;
   (d) precipitating the crude polysaccharide from the treated liquid medium with a sufficient amount of a water-miscible lower alkanol.

4. A process of claim 1 wherein steps (c) and (d) are:
   (c) digesting the cell paste from step b with an enzyme to obtain a liquid extract;
   (d) precipitating the crude polysaccharide from the liquid extract from digested cell paste with a sufficient amount of a water-miscible lower alkanol.

5. A process of claim 1 further comprising:
   (h) eluting the resolubilized semi-purified polysaccharide of step (g) in a liquid medium through a gel column to obtain the purified polysaccharide.

6. The process of claim 1 wherein the fermentation medium contains sodium chloride, potassium phosphate dibasic, 2.5% by weight glucose, and the dialyzable constituents of soy bean and yeast extracts.

7. In a process for the preparation of an antigen type-specific polysaccharide of Group B Streptococcus wherein Group B Streptococcus bacteria types $I_a$, $I_b$, II, or III are grown in a high glucose, soy bean and yeast extract medium and crude polysaccharide in precipitated therefrom, the improvement which comprises suspending said crude polysaccharide in deionized water and adding thereto sufficient cationic detergent to precipitate the antigen type-specific polysaccharide.

8. The process of claim 7 wherein the cationic detergent is hexadecyltrimethylammonium bromide.

* * * * *

UNITED STATES PATENT AND TRADEMARK OFFICE
CERTIFICATE OF CORRECTION

PATENT NO. : 4,413,057
DATED : November 1, 1983
INVENTOR(S) : Carlo et al.

It is certified that error appears in the above—identified patent and that said Letters Patent is hereby corrected as shown below:

On the title page, col. 1, change "Appl. No.: 343,305" to --Appl. No.: 240,290--.

Signed and Sealed this

Fifth Day of June 1984

[SEAL]

Attest:

GERALD J. MOSSINGHOFF

Attesting Officer

Commissioner of Patents and Trademarks